US009110030B2

(12) United States Patent
Kerschensteiner (10) Patent No.: US 9,110,030 B2
(45) Date of Patent: Aug. 18, 2015

(54) COLORIMETRIC GELATINASE ASSAY (71) Applicant: Daniel A. Kerschensteiner, Kernersville, NC (US)

(72) Inventor: Daniel A. Kerschensteiner, Kernersville, NC (US)

( * ) Notice: Subject to any disclaimer, the term of this patent is extended or adjusted under 35 U.S.C. 154(b) by 0 days.

(21) Appl. No.: 13/932,366

(22) Filed: Jul. 1, 2013

(65) Prior Publication Data
US 2014/0004546 A1 Jan. 2, 2014

Related U.S. Application Data (60) Provisional application No. 61/690,531, filed on Jun. 29, 2012.

(51) Int. Cl.
*G01N 33/558* (2006.01)
*G01N 33/58* (2006.01)
*G01N 21/78* (2006.01)

(52) U.S. Cl.
CPC .............. *G01N 21/78* (2013.01); *G01N 33/558* (2013.01); *G01N 33/587* (2013.01); *G01N 2333/96494* (2013.01)

(58) Field of Classification Search
CPC ......... G01N 1/00; G01N 21/00; G01N 21/75; G01N 21/78; G01N 33/48; G01N 33/53; G01N 33/58; G01N 33/585; G01N 33/587; G01N 33/54366; G01N 33/558; G01N 33/573; G01N 2333/00; G01N 2333/90; Y10S 435/00; Y10S 435/96; Y10S 435/97; Y10S 435/967; Y10S 435/969; Y10S 436/815; C12Q 1/00; C12Q 1/25; C12M 1/00; C12M 1/16; B82Y 5/00; C12Y 101/00
See application file for complete search history.

(56) References Cited

U.S. PATENT DOCUMENTS 5,310,647 A * 5/1994 Kerschensteiner ............... 435/4
6,534,320 B2 3/2003 Ching et al.
(Continued)

FOREIGN PATENT DOCUMENTS

WO    WO 89/11543 A1    11/1989
WO    WO 2005031351 A1 *  4/2005 ............. G01N 33/52
(Continued)

OTHER PUBLICATIONS

Biagini, R.E. et al. 2006. Rapid, sensitive, and specific lateral-flow immunochromatographic device to measure anti-anthrax protective antigen immunoglobulin G in serum and whole blood. Clinical and Vaccine Immunology 13(5):541-546. specif. p. 542.*
(Continued)

*Primary Examiner* — John Brusca
*Assistant Examiner* — Sharon M Papciak
(74) *Attorney, Agent, or Firm* — Oblon, McClelland, Maier & Neustadt, L.L.P.

(57) ABSTRACT

The present invention is drawn toward a lateral-flow, colorimetric, gelatinase assay including a sample pad, a reagent pad, a membrane, and an absorbent pad, in that order, wherein the reagent pad has therein a dried form of gelatin-coated nanoparticles in a salt and sugar matrix, and wherein the membrane portion has a test stripe and a control stripe, such that the test stripe is a solution of electrolyte evaporated into a layer, and the control stripe is a solution of anti-gelatin antibody evaporated into a layer. The present invention is also drawn toward a method of detecting one or more gelatinases in a sample fluid using the assay, and methods of determining treatment for wound healing, cancer, ocular rosacea, periodontal disease and equine arthritis using the assay.

19 Claims, 3 Drawing Sheets

From left: Tube 1=starting material
Tube 2: After exposure with gelatinase
Tube 3: Tube 2 After 1 hour; note ppt.

(56) References Cited

U.S. PATENT DOCUMENTS

| | | |
|---|---|---|
| 2002/0142485 A1 | 10/2002 | Liu et al. |
| 2010/0273666 A1 | 10/2010 | Bernatchez et al. |
| 2011/0039805 A1 | 2/2011 | Pflugfelder et al. |
| 2012/0156804 A1 | 6/2012 | Tan et al. |

FOREIGN PATENT DOCUMENTS

| | | | | |
|---|---|---|---|---|
| WO | WO 2008/075056 A1 | 6/2008 | | |
| WO | WO 2009/105786 A2 | 8/2009 | | |
| WO | WO 2011031573 A1 * | 3/2011 | ............... | C12Q 1/37 |
| WO | WO 2012/040331 A2 | 3/2012 | | |
| WO | WO 2012/071145 A1 | 5/2012 | | |

OTHER PUBLICATIONS

Kolosova, A.Y. et al. 2007. Development of a colloidal gold-based lateral-flow immunoassay for the rapid simultaneous detection of zearalenone and deoxynivalenol. Analytical and Bioanalytical Chemistry 389:2103-2107. specif. pp. 2103, 2105.*

Clegg, P.D. et al. 1998. The effect of drugs commonly used in the treatment of equine articular disorders on the activity of equine matrix metalloproteinase-2 and 9. Journal of Veterinary Pharmacology and Therapeutics 21:406-413. specif. pp. 406-407.*

Krizkova, S. et al. 2011. Assays for determination of matrix metalloproteinases and their activity. Trends in Analytical Chemistry 30(11): 1819-1832. specif. pp. 1819, 1828.*

International Search Report and Written Opinion issued Dec. 3, 2013, in PCT/US13/48908 filed Jul. 1, 2013.

M. Sakaguchi, et al., "Specific IgE and IgG to gelatin in children with systemic cutaneous reactions to Japanese encephalitis vaccines", Allergy, 2001, vol. 56, pp. 536-539.

Sally D. Solomon, et al., "Synthesis and Study of Silver Nanoparticles", Journal of Chemical Education, vol. 84,No. 2, Feb. 2007, pp. 322-325.

* cited by examiner

From left: Tube 1=starting material
Tube 2: After exposure with gelatinase
Tube 3: Tube 2 After 1 hour; note ppt.

COLORIMETRIC GELATINASE ASSAY

CROSS-REFERENCE TO RELATED APPLICATIONS

This application claims priority to U.S. provisional application No. 61/690,531 (filed Jun. 29, 2012), and incorporates herein by reference said provisional application.

BACKGROUND OF THE INVENTION

Proteases are enzymes that act on proteins by breaking them down into peptides and amino acids. A gelatinase is a type of protease that hydrolyzes gelatin into peptides and amino acids. Recently, specific gelatinases have been found to be present in elevated amounts in the wound exudates of patients with non-healing wounds, in the urine of cancer patients, in the tears of ocular rosacea patients, in the saliva of patients with periodontal disease, and in the synovial fluid of horses suffering from equine arthritis.

The current primary technique for the detection of gelatinases in a sample is gelatin zymography. Gelatin zymography is an electrophoretic technique for the detection of gelatin-hydrolytic enzymes, i.e., gelatinases. However, gelatin zymography requires laborious, skillful and time-consuming (about one week) lab work. Thus, for most hospitals, medical professionals, and other care-providing facilities, evaluation of gelatinase activity is not feasible.

Accordingly, a point-of-care gelatinase test would be an innovation in the fields of caring for wounds, cancer, ocular rosacea, periodontal disease and equine arthritis. Such a point-of-care gelatinase test may help health care providers to make informed decisions about which treatment is or is not appropriate. Advantages of guiding therapy in this way may include avoidance of unnecessary interventions, reduced nursing time, fewer clinic visits, shorter overall treatment duration, earlier recognition and prevention of complications, improved quality of life, faster healing and earlier return to work.

These potential benefits may lead regulators in the future to require such a point-of-care test before the use of specific treatments. Monitoring gelatinases through weekly testing with cheap, disposable, colorimetric tests, may allow health care providers to recognize whether care is effective and, therefore, whether the current treatment/approach is appropriate.

Lateral flow tests are simple devices intended to detect the presence of an analyte in a sample without the need for specialized and costly equipment. Typically, these tests are used for medical diagnostics either for home testing, point-of-care testing, or laboratory use. A well-known application of it is the home pregnancy test. Although commonly employing immunochromatographic techniques which take advantage of the monovalent specificity of the antibody-antigen reaction, the tests using them typically only measure one analyte, for example hCG in the case of pregnancy tests. Although tremendous efforts have been made in developing and commercializing lateral flow immunochromatographic assays for detecting a large number of analytes, minimal work has been done in adapting the lateral flow assay format for detecting enzyme activity. Thus, such a lateral flow assay format for detecting gelatinase activity that is cheap, disposable, and colorimetric-based would be an innovation.

BRIEF SUMMARY OF THE INVENTION

The present invention relates to a sensitive, rapid, one-step, quantitative and colorimetric gelatinase activity assay test that can be used at the point of care and that can be used, for example, to assess whether a wound is healing or not, whether a patient is likely suffering from cancer, ocular rosacea or periodontal disease, and whether a horse is likely suffering from equine arthritis. The test of the present invention also measures multiple gelatinases, not just one specific gelatinase, in providing the aforementioned assessments.

DETAILED DESCRIPTION OF THE INVENTION

The present invention relates to an innovative, quantitative and colorimetric gelatinase activity assay that can be used to assess whether a wound is healing or not, whether a patient is likely suffering from cancer, ocular rosacea or periodontal disease, and whether a horse is likely suffering from equine arthritis.

Wound Healing Diagnosis Using Wound Exudate

In wound healing, the major proteases are the matrix metalloproteinase (MMPs) from fibroblasts, namely MMP-2 and MMP-9 (i.e., gelatinases), and the serine proteases, namely leukocyte elastase. In the normal wound healing process, proteases break down damaged extracellular matrix proteins and foreign material so that new tissue can form and wound closure can occur in an orderly fashion. However, when the level of protease activity is too high the delicate balance between tissue breakdown and repair is disturbed. A chronic and non-healing wound is the result.

Figure 1:
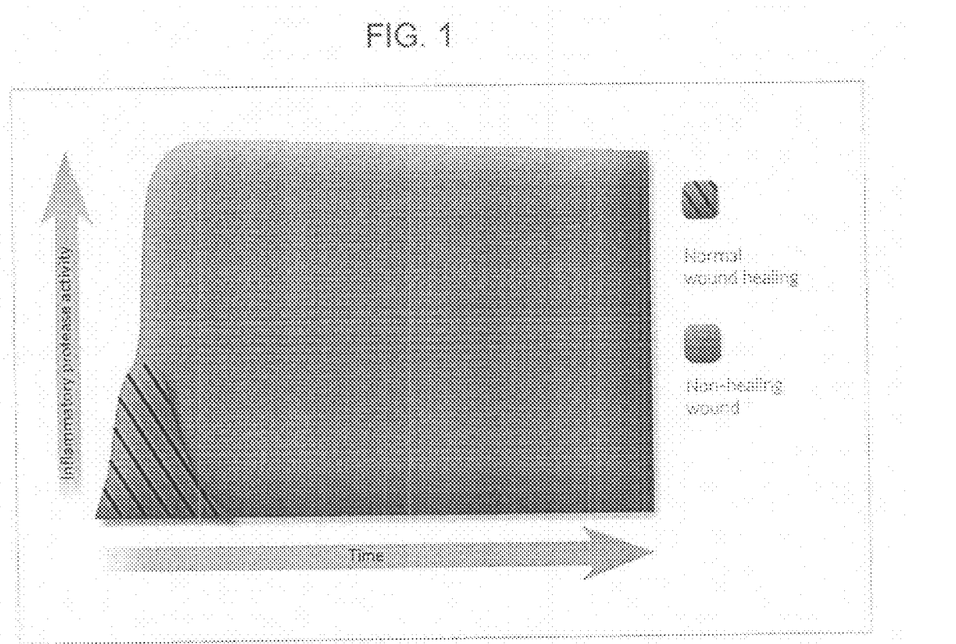
FIG. 1 illustrates changes in protease/gelatinase activity in normal wound healing and non-healing wounds.

In the normal course of wound healing, there is a rapid initial increase in protease levels, including the gelatinases of MMP-2 (EC 3.4.24.24) and MMP-9 (EC 3.4.24.35). The levels peak at about day three and start to reduce by about day five. In non-healing wounds, however, not only do the proteases/gelatinases reach higher levels than in healing wounds, but they persist far longer. See FIG. 1. The result is a highly destructive wound environment. Data to date suggest that proteases, including the gelatinases of MMP-2 and MMP-9, may be the most promising biomarkers for assessing wound healing at the biochemical level. However, currently it is very difficult to assess the level of proteases/gelatinases in wounds.

Research studies have analyzed types, levels and activities of proteases/gelatinases in wound fluid derived from biopsies obtained in laboratory conditions. The results of these studies show a consistent trend of low levels of protease/gelatinase activity in healing wounds, and high levels in stalled or poorly healing wounds that decrease when the wounds begin to heal.

Estimates of some 5.7 million Americans, afflicting notably the elderly, diabetics and the obese, have hard-to-heal wounds estimated to cost $25 billion annually in chronic wound care alone. As stated by Serena et al. (Protease Activity Levels Associated with Healing Status of Chronic Wounds, Poster (2011), Wounds UK), there is a "need to measure multiple proteases in order to determine if proteolytic activity is causing a problem in the wound and preventing it from healing." As also noted in *International Consensus*: "The Role of Proteases in Wound Diagnostics" (An expert working group review, London, Wounds International, 2011), "a protease test kit at the point of care could change wound care world-wide."

Cancer Diagnosis Using Urine

Matrix metalloproteinases (MMPs) are a class of proteolytic enzymes that are involved in tumor invasion and metastasis in many types of human carcinomas. Elevated levels of MMPs have been found in serum of animals bearing tumors and in cancer patients. In a recent study of enzyme activity using substrate zymography, it was discovered that functional MMPs lysing gelatin were in the urine of those with various cancers compared to age-matched individuals with normal health. More specifically, the findings showed that not only cancers of the genitourinary tract (e.g., cancers of the prostate, bladder, ovaries and kidney), but also cancers distant from the genitourinary tract (e.g., cancers of the brain and breast), displayed biologically active gelatinases in their urine, namely the gelatinases of MMP-2 and MMP-9.

Ocular Rosacea Diagnosis Using Tears

Rosacea is a relatively common, chronic skin disorder believed to affect 14 million Americans. In some cases, rosacea may be associated with certain eye disorders. Ocular rosacea is described as an inflammatory eye condition that roughly 82% of patients with facial rosacea have concurrently. In sever ocular rosacea, there may be corneal ulceration/infection which, if untreated, may even lead to perforation of the eye, and it can be a potentially blinding complication. Timely diagnosis is very important for long-term ocular health.

It has been established that matrix metalloproteinases (MMPs) are implicated in the breakdown of the proteins in the eye of ocular rosacea patients. The corneal epithelium produces gelatinase B (i.e., MMP-9) in higher amounts in ocular rosacea patients, an enzyme that participates in the wound healing process. The 84-kDa active form of MMP-9 is not observed in normal tear fluid, only in the tear fluid of ocular rosacea patients. This suggests that MMP-9 measurement may enable early diagnosis of ocular rosacea which would lead to treatments to prevent sight-threatening corneal complications. Currently, the assay of the small concentrations of MMP-9 activity in the small tear fluid volumes obtained is performed by means of sophisticated research-only assays such as ELISA, which is a technology that is not suitable for routine point-of-care evaluation.

Periodontal Disease Diagnosis Using Saliva

Proteolytic enzymes are associated with the tissue destruction in periodontal diseases. Matrix metalloproteinases (MMPs) like MMP-2 and MMP-9 have the primary role in this process, since, in concert, they can degrade most of the extracellular matrix components. It has been found that periodontitis patients have significantly higher levels of MMP-9 in their saliva than healthy subjects. Also, MMP-2 is elevated in periodontitis patients. Periodontal treatment has been shown to reduce the amount of these gelatinases dramatically. Thus, MMP-2 and MMP-9 clearly participate in tissue destruction in periodontitis.

Equine Arthritis Diagnosis Using Synovial Fluid

Horses are valuable animals to their owners and they frequently come up lame. In horses, the synovial fluid functions like the oil lubricating the ball bearings which are the joints of the horse. Recent analysis using gelatin zymography indicates that the amount of gelatinases MMP-2 and MMP-9 is significantly elevated in the synovial fluid of horses with arthritis (e.g., aseptic joint disease, septic arthritis), but MMP-2 and MMP-9 are absent from the synovial fluid of non-arthritic horses.

Accordingly, the specific gelatinases of MMP-2 and MMP-9 are of interest in the present invention as they have been found to be present in elevated amounts in each of: wound exudates of patients with non-healing wounds, urine of cancer patients, tears of ocular rosacea patients, saliva of patients with periodontal disease, and the synovial fluid of horses suffering from equine arthritis. Thus, the following three embodiments of the present invention are drawn toward colorimetric assay tests for the detection of both the MMP-2 and the MMP-9 gelatinases.

First Embodiment

Lateral Flow

The first embodiment of the present invention relates to a lateral flow-based, colorimetric, gelatinase (MMP-2 and MMP-9) assay test. The assay contains at least the following four elements: a sample pad, a reagent pad, a membrane, and an absorbent pad, in that order.

The first element, i.e., the sample pad, has the capacity to transport fluid spontaneously and passively by capillary action. The sample pad draws up a volume of sample fluid obtained from, for example, wound exudate, urine, tears, saliva and equine synovial fluid.

The sample pad can be made of, for example, woven meshes and cellulose filters such as porous paper. Woven meshes, sometimes called screens, normally work very well to distribute the sample volume evenly to the reagent pad. They also typically have good tensile strength and handle well, even when wet. Meshes have very low bed volumes, meaning that they retain very little sample volume, normally 1-2 $\mu L/cm^2$. On the other hand, it is impractical to treat them with the intention of loading them with enough solutes to modify protein content, pH, ionic strength or viscosity of the test sample. Meshes can also be expensive relative to other porous media.

On the other hand, cellulose filters have properties that are nearly the opposite of woven meshes. They are thick (>250 $\mu m$), weak, and relatively inexpensive. Cellulose filters also have large bed volumes (>25 $\mu L/cm^2$). Cellulosic filters are especially preferred for testing urine samples. When using cellulose filters, care must be taken to ensure sufficient and consistent contact with the reagent pad. Failure to achieve good contact can lead to interrupted or inconsistent transfer of fluid into the reagent pad.

The length and width of the sample pad are not particularly limited, however they preferably provide a sample pad area of about 3 to 7 $cm^2$, more preferably about 5 $cm^2$. The thickness of the sample pad is typically about 300 to 1000 $\mu m$, preferably about 500 to 750 $\mu m$.

In this embodiment of the present invention, once the sample pad is sufficiently soaked with sample fluid, the sample fluid migrates to the second element.

The second element, i.e., the reagent pad, has the capacity to transport fluid spontaneously and passively by capillary action like that of the sample pad, and can be made of, for example, woven meshes and cellulose filters like that of the sample pad. However, unlike the sample pad, the reagent pad contains therein a dried form of gelatin-coated nanoparticles in a salt/sugar matrix. The nanoparticles of the gelatin-coated nanoparticles can be, for example, colloidal gold nanoparticles and colloidal silver nanoparticles.

A buffer can be used for applying the nanoparticles to the reagent pad. The recommended buffer for colloidal gold particles is 2 mM borate at pH 7, supplemented with 1% to 10% sucrose or trehalose. The borate provides buffer control and also has a slight surfactant quality that aids in resolubilization of the particles. The sucrose (or trehalose) serves as a preservative and a resolubilization agent. When the nanoparticles are dried in the presence of sugar, the sugar molecules form a layer around the particles that helps to stabilize the biological structures. When the sample enters the reagent pad, the sugar molecules instantaneously dissolve, carrying the particles away from the surface and into the fluid stream.

The particular nature of loading the reagent pad will be dictated by the format of the supply, and several variations are possible. One such variation includes a method wherein, to treat the material, a flat container should be filled with enough detector particle solution to allow submersion. The size of the container and the depth of solution used should be considered in advance to allow for ease of handling without using a large excess of solution. The pad material should be dipped in the solution and held up to allow all excess to run back into the pan. The material should then be laid flat on a nonabsorbent surface for drying. To maximize the performance of the detector particle, the treated reagent pad needs to be dried as quickly and completely as possible. Such drying options include, for example, air drying, heated drying, freeze drying and vacuum drying.

The length and width of the reagent pad are not particularly limited, however they preferably provide a reagent pad area of about 1 to 3 cm$^2$, more preferably about 2 cm$^2$. The thickness of the reagent pad is typically about 300 to 1000 μm, preferably about 500 to 750 μm.

In this embodiment of the present invention, once the sample fluid dissolves the salt-sugar matrix and solubilizes the nanoparticles within the reagent pad, the mixture enters into the third element of the assay.

The third element, i.e., the membrane must irreversibly bind capture reagents at the test and control lines. Preferably, the membrane is a porous, synthetic, polymeric membrane. The polymer from which the membrane is made determines most of its binding characteristics. If the membrane undergoes a secondary process that chemically alters the polymer or buries it under a second polymer, protein binding properties may be dramatically altered. Typical polymers for the membrane include, for example, nitrocellulose, polyvinylidene fluoride, (charged modified) nylon, and polyethersulfone; with nitrocellulose being preferred.

Nitrocellulose membranes bind proteins electrostatically through interaction of the strong dipole of the nitrate ester with the strong dipole of the peptide bonds of the protein. Nitrocellulose membranes are completely neutral with no acidic protons. Although their ability to adsorb protein is independent of the pH of the immobilization solution, pH can affect the immobilization efficiency of a particular protein by altering its properties in solution. When applying capture reagents to nitrocellulose membranes, chaotropic agents should be omitted or used at concentrations <0.01% v/v. These compounds can physically interfere with molecular contact between the protein and nitrocellulose. If included in the capture reagent buffer during manufacture, the signal may start to develop when the test stripe is run and then disappear as the capture reagent lifts off the nitrocellulose and migrates downstream. If chaotropic reagents are required to prevent non-specific interactions or reduce background, they should be put into the sample pad. It is important to recognize that the capture reagent will be localized at the test stripe because it is evaporated in place, but this fact does not imply that the protein is actually adsorbed to the nitrocellulose at the molecular level.

The membrane contains two areas separated at a distance in linear sequence where molecules have been immobilized to signal any positive result (i.e., the test stripe), and to signal that the test is performing well (i.e., the control stripe). In this application, the test stripe consists of a solution of an electrolyte evaporated into a layer. The electrolyte can be any soluble electrolyte which will flocculate the nanoparticles of the reagent pad, for instance, Na, Al, K, etc, with $CaCl_2$ being the preferred electrolyte for flocculating colloidal gold. The control stripe of the membrane is a solution of anti-gelatin antibody evaporated in a layer positioned just beyond/after the test stripe. The test stripe and the control stripe are typically about 1 mm wide.

The length and width of the membrane are not particularly limited, however they preferably provide a membrane area of about 1 to 7 cm$^2$, more preferably about 3 to 5 cm$^2$. The thickness of the membrane is typically about 300 to 1000 μm, preferably about 500 to 750 μm.

In the membrane, a portion of the gelatin-coated nanoparticles are subjected to enzyme action of any gelatinases present in the fluid sample and are then capable of being flocculated by the electrolyte, e.g., $CaCl_2$. The particles will deposit at the test stripe as a colored agglutination or a visible flocculation of particles. After a while, when more and more fluid has passed over the test stripe, the enzyme-reacted nanoparticles accumulate and the test stripe area changes color that is proportional to the total amount of gelatinase activity in the fluid sample. The remaining gelatin-coated nanoparticles, either not reacted by enzyme in the time allowed by the assay conditions, or because there is little or no gelatinase in the sample, continue to move on with the solvent front. These remaining particles will be ultimately captured in the antigelatin control stripe as a colored line indicating that all is well with the procedure. The chemistry that occurs in the membrane element of the inventive assay will be described in greater detail below.

In this embodiment of the assay of the present invention, once the sample fluid has migrated through the entirety of the membrane, the spent sample fluid enters into the fourth element of the assay where excess fluid collects.

The fourth element, i.e., the absorbent pad, is wicking in nature and collects the spent/excess sample fluid of the assay. Like the sample pad, the absorbent pad can be made of, for example, woven meshes and cellulose filters such as porous paper. The length and width of the absorbent pad are not particularly limited, however they preferably provide a absorbent pad area of about 2 to 6 cm$^2$, more preferably about 4 to 5 cm$^2$. The thickness of the absorbent pad is typically about 300 to 1000 μm, preferably about 500 to 750 μm.

It should be noted here that the above-discussed four "elements" are discrete units of the lateral flow assay that can be separated by a varying degree of space or that can be touching, or even overlapping, one another (i.e., no space therebetween). If the elements are separated by a varying degree of space, said space cannot be so large as to prohibit the migration/wicking of the sample fluid from one element to the next. Alternatively, the four "elements" can be instead considered as four "zones" of a single, contiguous unit, for example, a single capillary pad that has four individually treated zones to reflect the individual nature of the above-discussed four "elements."

Chemistry of the Membrane Element

The assay of the present invention utilizes a gelatinase reagent. Gelatin is derived from collagen and is the most abundant connective tissue protein that makes up the dermal layer. Pure gelatin chemisorbs onto the surface of metallic colloid nanoparticles as a result of hydrophobic interactions. In so doing, gelatin "protects" any negatively charged colloid from the effects of charge reversal by electrolyte flocculation by shielding the entirety of surface charges. Thus, a concentration of electrolyte that will flocculate a quantity of bare metallic colloid, for example gold colloid, with the appearance of a red-to-grey color change (in the case of gold colloid) will not affect the same quantity of metallic colloid chemisorbed with protecting amounts gelatin—under these conditions the gelatin-coated colloid remains red (in the case of gold colloid). According to one theory, gelatin does this by forming loops on the surface of the nanospheres of metallic colloids in a "VW" pattern, where the gelatin is adsorbed to the surface of the colloid at hydrophobic areas represented by the points and ends of the "V" and "W", while the hydrophilic areas are freely unattached. Gelatin does this quite efficiently. Gelatin is more effective in protecting metallic colloid nanoparticles from flocculation on a molar basis than any other natural substance examined. The concentration of gelatin (100 kDa) needed to accomplish this protection is miniscule, for example 10-20 picomol/ml, preferably 12-18 picomo/ml, most preferably only 16.6 picomol/ml of 3.2 nm, 20 microgram/ml metallic colloid nanoparticles.

Gelatinases hydrolyze the gelatin on the surface of the nanoparticles, resulting in the loss of gelatin's integral structure as it abolishes its protection against charge reversal by the electrolyte. Once hydrolyzed into polypeptides enzymatically, electrolytes act on the now unprotected negatively-charged colloid and flocculate it, changing color in proportion to the enzyme concentration. As with any catalysis, the products formed in time are a fraction of the whole gelatin nanoparticle. The rate of flocculation results in a change of turbidity of light in the suspended nanoparticles that can be followed by using an inexpensive nephelometer. The degree of flocculation can be directly correlated with the quantity of gelatinases in the sample fluid.

The assay described is very sensitive to the measurement and quantification of gelatinases. A standard curve can be constructed in which a measure of turbidity is linear from 15 to 1000 nanograms of purified trypsin with 5 minutes incubation time. In practice, pig skin gelatin is titrated to a fixed amount of 3.2 nm, 20 ppm nanoparticles at an elevated pH to maximize the hydrophobic attraction onto the particles. $CaCl_2$ is added at a concentration which would ordinarily flocculate bare uncoated nanoparticles, but doesn't have any effect on the gelatin-coated nanoparticles. When the gelatin-protected nanoparticles are exposed briefly to a dilute solution of protease, some of the gelatin is hydrolyzed into polypeptides exposing some of the negative charges on the nanoparticles. Those nanoparticles with exposed negative charges as a result of enzymatic action will be flocculated by $CaCl_2$ (or any other electrolyte) by charge reversal. This phenomenon works in place of the antibody-to-cognate antigen which is frequently seen in the construction of the lateral flow device. It also detects all of the gelatinases that hydrolyze gelatin, not just a single protease which is the case with an immunocognate. Furthermore, not only is the assay rapid, but the assay is very sensitive, for example, approximately 15 nanograms is the detection limit for a model enzyme that hydrolyses gelatin, namely purified trypsin.

Figure 2A:
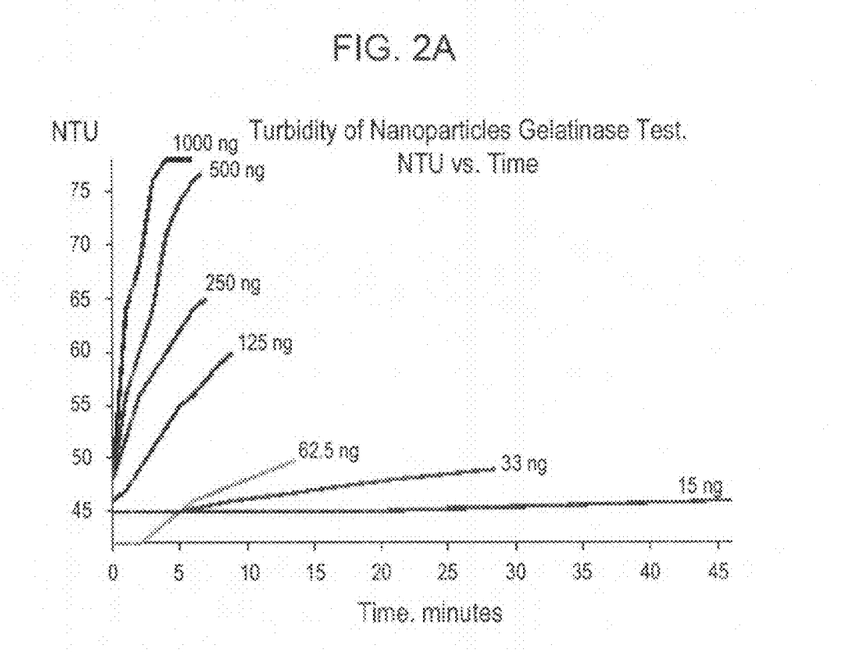
FIG. 2A illustrates the time course of flocculation with trypsin-measured turbidity (i.e., NTU vs. minutes).
Figure 2B:
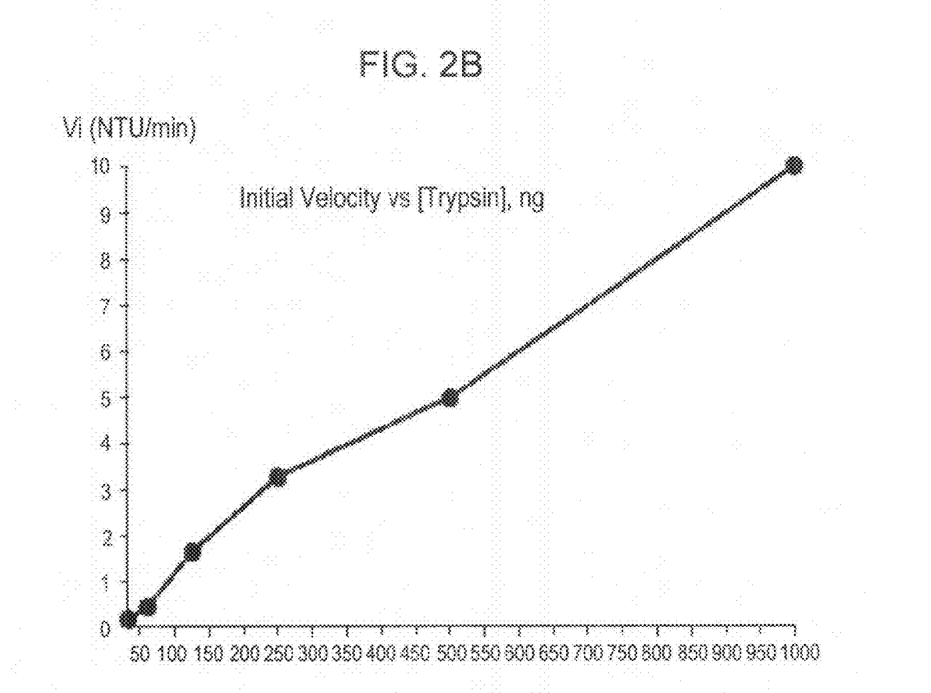
FIG. 2B illustrates the standard curve of initial velocity versus trypsin concentration (i.e., NTU/minute vs. nanograms of trypsin).

The enzymes of interest in the present invention are those that are able to hydrolyze gelatin and therefore are capable of signaling a change of color and an increase in turbidity when reacted with the inventive assay. A kinetic study reacting aliquots of trypsin with 2 ml of gelatin-colloidalAu—$CaCl_2$ in a turbidimeter showed that small amounts (e.g., nanograms) of a pure gelatinase could be quantitated in a drop of fluid (i.e., approximately 0.025 ml) within 15 minutes at room temperature using a simple instrument. The standard curve noted above is used and is linear with the initial velocity of the turbidity reading. See FIGS. 2A and 2B. Any gelatinase found in a sample fluid can be quantified using this standard curve and a turbidity reading from, for example, an inexpensive nephelometer.

U.S. Pat. No. 5,310,647 is incorporated herein by reference and provides additional information relating to the above-mentioned nanoparticles, flocculation, turbidity changes, etc.

Second Embodiment

Microwell Strip

The second embodiment of the present invention is a microwell strip-based embodiment. While metallic colloids of varying kinds can be used in this embodiment (e.g., silver colloid, gold colloid, etc.), colloidal gold will be discussed in the description of this embodiment as an exemplary metallic colloid. The scope of this embodiment is not limited to colloidal gold.

Colloidal gold is manufactured reproducibly and inexpensively at room temperature without use of dispersals which facilitates coating with gelatin. The metal hydrosol is prepared at room temperature in a size range of 50-55+/−2 nm and has an intense ruby red coloration. Any larger particle size and the color violet making any blue color from flocculation less distinguished. Recombinant human gelatin (from Fibro-Gen, 100 kD) is bloomed and melted in buffer at 50° C. then chemititrated at different pH levels onto the particles. This produces the lowest detection limit. Finally, additives such as enzyme cofactors and flocculant aids at optimal ionic strength and pH are incorporated to produce the most sensitive test for gelatinase-cleaving enzymes.

The assay test product of this embodiment consists of four items: one dropper bottle of gelatin-colloidal gold and another containing diluent in 10 ml polypropylene bottles, a collection device (e.g., a swab) for collecting sample fluid (e.g., wound exudate, urine, tears, saliva, equine synovial fluid) and a strip of 8-microwells (0.5 ml capacity). The sample fluid is weighed and then diluted in one ml of diluent. The diluent can be, for example, Ringer's solution, phosphate-buffered saline or sterile saline. A pressure/filtration step can be used to remove gross debris if needed. The sample is then serially diluted 8-fold from 0 to 128 in a standard 8-place 0.5 ml microwell strip. That is, a starting volume taken from the sample fluid already diluted with one ml of diluent is the first sample followed by 1:2, 1:4, 1:8, 1:16, 1:32, 1:64, and 1:128 sample fluid dilutions. The starting volume can vary but is preferably 0.2 ml in this case due to the 0.5 ml capacity of the microwells of the microwell strip. An equal volume of testing reagent (e.g., gelatin-colloidal gold), equal to the starting volume, is added and stirred and allowed to react for 10 to 20 minutes, preferably 15 minutes. After that period of time, the highest dilution which changes color is the dilution or titer of the gelatinase concentration in the sample fluid (e.g., wound exudate, urine, tears, saliva, equine synovial fluid).

When this embodiment is used in wound healing diagnosis, the titer will be low initially and decline over time for healing wounds and the titer will be high initially and it will persist at a higher level (titer) for those wounds which fail to heal.

Third Embodiment

Whole Tube

The third embodiment of the present invention is a whole tube-based embodiment. While metallic colloids of varying kinds can be used in this embodiment (e.g., silver colloid, gold colloid, etc.), colloidal silver will be discussed in the description of this embodiment as an exemplary metallic colloid. The scope of this embodiment is not limited to colloidal silver.

Figure 3:
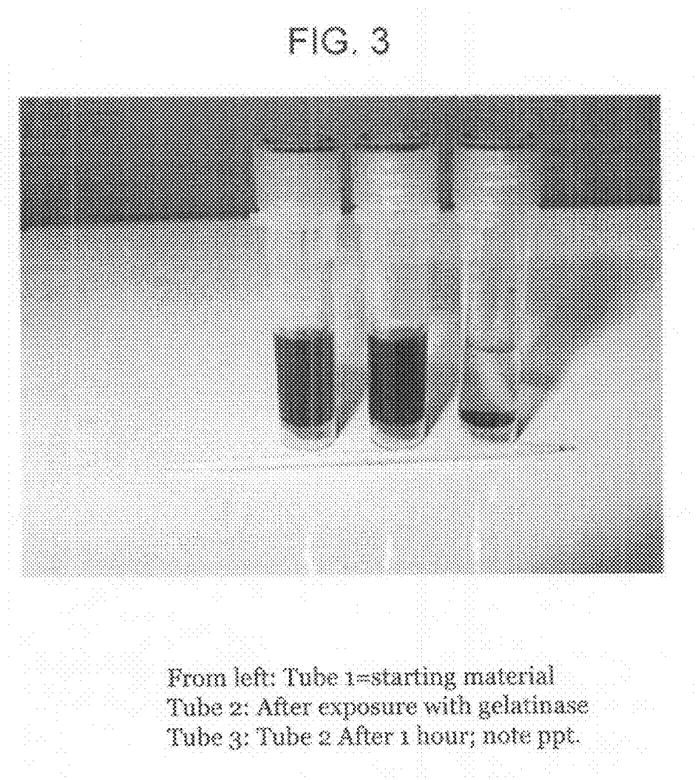
FIG. 3 illustrates the visual appearance of the results of an assay run according to the third embodiment of the present invention.

Beef gelatin, colloidal silver (300 ppm from Purest Colloids, NJ) and electrolyte buffers are chemititrated in the same manner as described above in the second embodiment. The mixture is contained in individual microvials of 1-2 ml capacity which have been previously treated with a siliconizing agent (e.g., Rain-X). The sample fluid (e.g., a wound, urine, tears, saliva, equine synovial fluid) collector in this embodiment is a dot of paper made from punching out a circle from absorbent paper. In this case, the circle of paper has only so much capacity to hold liquid (e.g., about 0.1 ml). It is removed from the sample fluid and placed into a microvial containing the gelatin-collidal silver which has a yellow color. The vial is capped; contents shaken and the reaction begins. The concentration of human gelatin required to critically protect the sol from salt flocculation (CPC) based on preliminary studies of the technology is vanishingly small, for example, 50 µg or 1 mM per ml of colloidal silver. The protective integral structure of gelatin is reduced into smaller sized polypeptides by the small numbers of rapidly catalyzed cleavages, destroying the protective structure surrounding the metallic nanoparticles. The silver particles then agglomerate, with the silver sol passively changing its appearance to black which is visibly apparent in 10 to 20 minutes, preferably 15 minutes. See FIG. 3.

Enzymes

The enzymes used in the above-described embodiments of the present invention are not limited so long as they can hydrolyze gelatin. Thus, it is the function of the enzymes (i.e., their ability to hydrolyze gelatin) that determines their sufficiency for use in the assays of the present invention and not their structure. Nevertheless, the present invention identifies two specific exemplary enzymes that can be used in the assays of the present invention, namely MMP-2 (EC 3.4.24.24) and MMP-9 (EC 3.4.24.35). While MMP-2 and MMP-9 are examples of gelatinases that hydrolyze gelatin, the present invention is not limited to said gelatinases and is not limited to enzymes having the same or similar structure as that of said gelatinases.

Nomenclature

In the context of the present invention, the term "about", when referring to, for example, amounts and dimensions, refers to a variance of +/−10% or less, preferably +/−5% or less, more preferably +/−2% or less, and most preferably +/−1% or less.

The invention claimed is:

1. A lateral-flow, colorimetric, gelatinase assay comprising a sample pad, a reagent pad, a membrane, and an absorbent pad, in that order, wherein:
    the reagent pad comprises therein a dried form of gelatin-coated nanoparticles in a salt and sugar matrix, and
    the membrane comprises a test stripe and a control stripe, wherein the test stripe comprises a solution of electrolyte evaporated into a layer, and the control stripe comprises a solution of anti-gelatin antibody evaporated into a layer.

2. The assay according to claim 1, wherein one or more of the sample pad, the reagent pad and the absorbent pad are a woven mesh or a cellulose filter.

3. The assay according to claim 1, wherein one or more of the sample pad, the reagent pad and the absorbent pad are porous paper.

4. The assay according to claim 1, wherein the nanoparticles are colloidal gold nanoparticles or colloidal silver nanoparticles.

5. The assay according to claim 1, wherein the membrane is a porous, synthetic, polymeric membrane.

6. The assay according to claim 4, wherein the membrane is selected from the group consisting of nitrocellulose, polyvinylidene fluoride, nylon and polyethersulfone.

7. The assay according to claim 1, wherein the sample pad is configured to draw up a volume of sample fluid.

8. The assay according to claim 1, wherein the absorbent pad is configured to collect excess fluid.

9. The assay according to claim 1, wherein the electrolyte of the test stripe contains at least one selected from the group consisting of Na, Al, K and Ca.

10. A method of detecting one or more gelatinases in a sample fluid using the assay of claim 1, said method comprising:
    loading the sample pad with a sample fluid comprising wound exudate, urine, tears, saliva or equine synovial fluid,
    allowing the sample fluid to migrate from the sample pad to the reagent pad, through the reagent pad to the membrane, through the membrane and to the absorbent pad,
    verifying that the assay is working by visually inspecting the control stripe for a color change, and
    detecting the presence of the one or more gelatinases by visually inspecting the test stripe for a color change and a change in turbidity, the intensities thereof being proportional to the amount of gelatinase present in the sample fluid.

11. The method of claim 10, wherein the nanoparticles of the reagent pad are colloidal gold nanoparticles and the color change of the test stripe is a red to grey color change.

12. The method of claim 10, wherein the nanoparticles of the reagent pad are colloidal silver nanoparticles and the color change of the test stripe is a yellow to black color change.

13. The method of claim 10, wherein the sample fluid is allowed to migrate from the sample pad to the absorbent pad in no more than 15 minutes.

14. The method of claim 10, wherein the one or more gelatinases are selected from the group consisting of MMP-2 and MMP-9.

15. A method of determining treatment for wound healing using the assay of claim 1, said method comprising:
    loading the sample pad with a sample fluid comprising wound exudate,
    allowing the sample fluid to migrate from the sample pad to the reagent pad, through the reagent pad to the membrane, through the membrane and to the absorbent pad,
    verifying that the assay is working by visually inspecting the control stripe for a color change,
    detecting the presence of the one or more gelatinases by visually inspecting the test stripe for a color change, the intensity thereof being proportional to the amount of gelatinase present in the sample fluid,
    determining if the wound from which the wound exudate was obtained is a non-healing wound or a healing wound by comparing the resultant test stripe with a control, and
    providing treatment for a non-healing wound if the wound is determined to be a non-healing wound or providing treatment for a healing wound if the wound is determined to be a healing wound.

16. A method of determining treatment for cancer using the assay of claim 1, said method comprising:
    loading the sample pad with a sample fluid comprising urine,
    allowing the sample fluid to migrate from the sample pad to the reagent pad, through the reagent pad to the membrane, through the membrane and to the absorbent pad,
    verifying that the assay is working by visually inspecting the control stripe for a color change,
    detecting the presence of the one or more gelatinases by visually inspecting the test stripe for a color change, the intensity thereof being proportional to the amount of gelatinase present in the sample fluid,
    determining if the patient from which the urine was obtained has cancer by comparing the resultant test stripe with a control, and
    providing treatment for cancer if the patient is determined to have cancer.

17. A method of determining treatment for ocular rosacea using the assay of claim 1, said method comprising:
    loading the sample pad with a sample fluid comprising tears,
    allowing the sample fluid to migrate from the sample pad to the reagent pad, through the reagent pad to the membrane, through the membrane and to the absorbent pad,
    verifying that the assay is working by visually inspecting the control stripe for a color change,
    detecting the presence of the one or more gelatinases by visually inspecting the test stripe for a color change, the intensity thereof being proportional to the amount of gelatinase present in the sample fluid,
    determining if the patient from which the tears were obtained has ocular rosacea by comparing the resultant test stripe with a control, and
    providing treatment for ocular rosacea if the patient is determined to have ocular rosacea.

18. A method of determining treatment for periodontal disease using the assay of claim 1, said method comprising:
    loading the sample pad with a sample fluid comprising saliva,
    allowing the sample fluid to migrate from the sample pad to the reagent pad, through the reagent pad to the membrane, through the membrane and to the absorbent pad,
    verifying that the assay is working by visually inspecting the control stripe for a color change,
    detecting the presence of the one or more gelatinases by visually inspecting the test stripe for a color change, the intensity thereof being proportional to the amount of gelatinase present in the sample fluid,
    determining if the patient from which the saliva was obtained has periodontal disease by comparing the resultant test stripe with a control, and
    providing treatment for periodontal disease if the patient is determined to have periodontal disease.

19. A method of determining treatment for equine arthritis using the assay of claim 1, said method comprising:
    loading the sample pad with a sample fluid comprising equine synovial fluid,
    allowing the sample fluid to migrate from the sample pad to the reagent pad, through the reagent pad to the membrane, through the membrane and to the absorbent pad,
    verifying that the assay is working by visually inspecting the control stripe for a color change,
    detecting the presence of the one or more gelatinases by visually inspecting the test stripe for a color change, the intensity thereof being proportional to the amount of gelatinase present in the sample fluid,
    determining if the horse from which the synovial fluid was obtained has equine arthritis by comparing the resultant test stripe with a control, and
    providing treatment for equine arthritis if the horse is determined to have equine arthritis.

* * * * *